(12) United States Patent
Williams et al.

(10) Patent No.: US 6,410,700 B1
(45) Date of Patent: Jun. 25, 2002

(54) GLYCAN DERIVATIVES

(75) Inventors: Keith Leslie Williams; Nicolle Hannah Packer; Andrew Arthur Gooley; John William Redmond, all of New South Wales; Steven Lewis Ramsay, Brompton; Warren Charles Kett, New South Wales, all of (AU)

(73) Assignee: Macquarie Research Ltd., New South Wales (AU)

( * ) Notice: Subject to any disclaimer, the term of this patent is extended or adjusted under 35 U.S.C. 154(b) by 0 days.

(21) Appl. No.: 09/284,302

(22) PCT Filed: Oct. 8, 1997

(86) PCT No.: PCT/AU97/00676

§ 371 (c)(1),
(2), (4) Date: Dec. 7, 1999

(87) PCT Pub. No.: WO98/15566

PCT Pub. Date: Apr. 16, 1998

(30) Foreign Application Priority Data

Oct. 8, 1996 (AU) .............................................. P02840

(51) Int. Cl.$^7$ .............................. C07H 5/04; C08B 37/00
(52) U.S. Cl. .................... 536/18.7; 536/55.2; 536/55.3; 536/124
(58) Field of Search .............................. 536/18.7, 55.2, 536/55.3, 124

(56) References Cited

U.S. PATENT DOCUMENTS 5,218,112 A  *  6/1993  Reardan et al. .............. 540/471
5,412,082 A  *  5/1995  Wittman et al. ............ 536/17.2

FOREIGN PATENT DOCUMENTS

WO   WO 96/19438   6/1996

OTHER PUBLICATIONS

Tronchet, J. et al. "Neoglycoproteines a sonde paramagnetique" Pharm. Acta Helv., vol. 67 No. 2 pp. 43–49.*
Borthakur, D. et al "Studies in cycloaddition reaction: Part XXXXVI" Indian J. Chem. vol. 27B pp. 724–725.*
Yoshioka, T. et al "Glycosides of N–hydroxy–N–arylamine derivatives" J. Chem. Soc., Perkin Trans. I pp. 1271–1276.*
Tronchet, J. et al "Hydroxyamino sugar derivatives" Naturforsch., B: Chem. Sci. vol. 47 No. 9 pp. 1341–1342.*
Evangelista, R.A. et al., "Acid–catalyzed reductive amination of aldoses with 8–aminopyrene–1,3,6–trisulfonate," *Electrophoresis* 17:347–351 (1996).
Suzuki, J. et al., "Assay of Urinary Free Fucose by FluorescenCe Labeling and High–Performance Liquid Chromatography," *Clin. Chem.* 38(5):752–755 (1992).
Kende, A.S. et al., "Controlled Reduction of Nitroalkanes to Alkyl Hydroxylamines or Amines by Samarium Diiodide," *Tetrahedron Letters*, 32(14):1699–1702 (1991).
Smith, Peter A.S. and Gloyer, Stewart E., "Equilibrium in the Behrend Rearrangement of Nitrones," *J. Org. Chem.* 40(17):2504–2508 (1975).
Dondoni, A., et al., "Stereoselective Aminohomologation of Chiral α–Alkoxy Aldehydes via Thiazole Additon to Nitrones. Application to the Synthesis of N–Acetyl–D–Mannosamine." Tetrahedron Letters, vol. 33, No. 29, pp. 4221–4224 (1992).
Paulsen, H., et al., "Darstellung von acyclischen und cyclischen Kohlenhydrat–Nitronen." Chem. Ber. No. 107, pp. 1998–2008 (1974). (Translation of abstract included).
Paulsen, Hans, et al., "Darstellung von acyclischen und cylischen Kohlenhydrat–Nitronen." Chem. Ber. 107, pp. 1998–2008 (1974) (contains English translation of Abstract).
Dondoni, Alessandro, et al., "Stereoselective Aminohomologation of Chiral α–Alkoxy Aldehydes via Thiazole Additional to Nitrones. Application to the Synthesis of N–Acetyl–D–Mannosamine." Tetrahedron Letters, vol. 33, No. 29, pp. 4221–4224 (1992).

* cited by examiner

*Primary Examiner*—James O. Wilson
*Assistant Examiner*—Leigh C. Maier
(74) *Attorney, Agent, or Firm*—Fish & Richardson P.C.

(57) ABSTRACT

Methods for producing glycan nitrones comprising reacting glycans with a mono-N-substituted hydroxylamine at pH 6 or greater to form glycan nitrones. Methods for producing glycan derivatives comprising reacting glycan nitrones produced by reacting glycans with a mono-N-substituted hydroxylamine at pH 6 or greater with a reducing agent to form hydroxylamine glycan derivatives and uses of the glycan nitrones and hydroxylamine glycan derivatives produced by the methods.

21 Claims, 17 Drawing Sheets

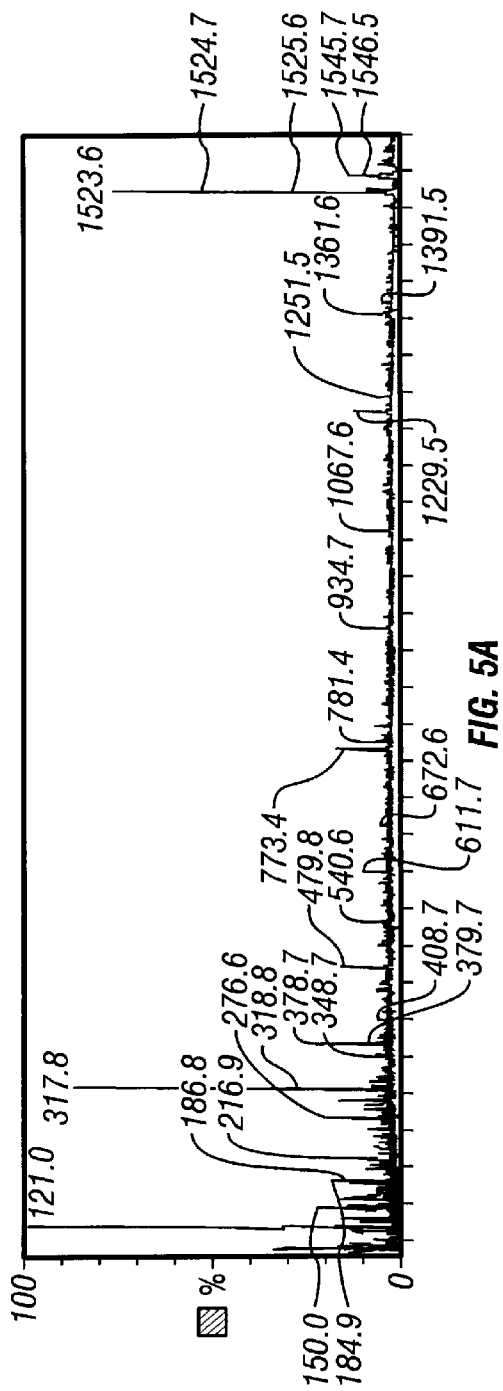
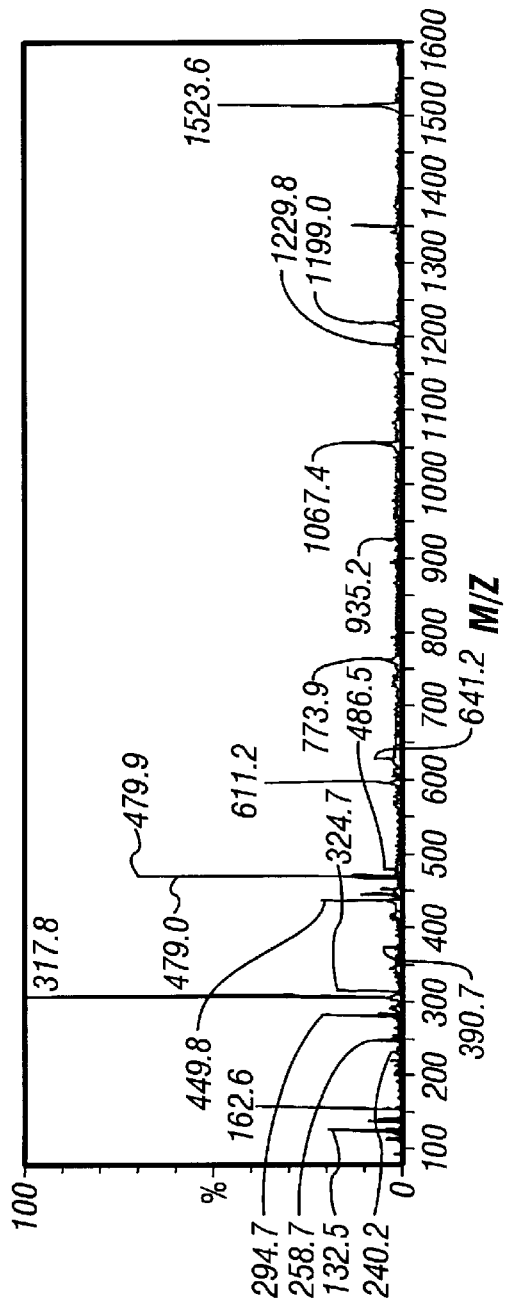
FIG. 5A
FIG. 5B

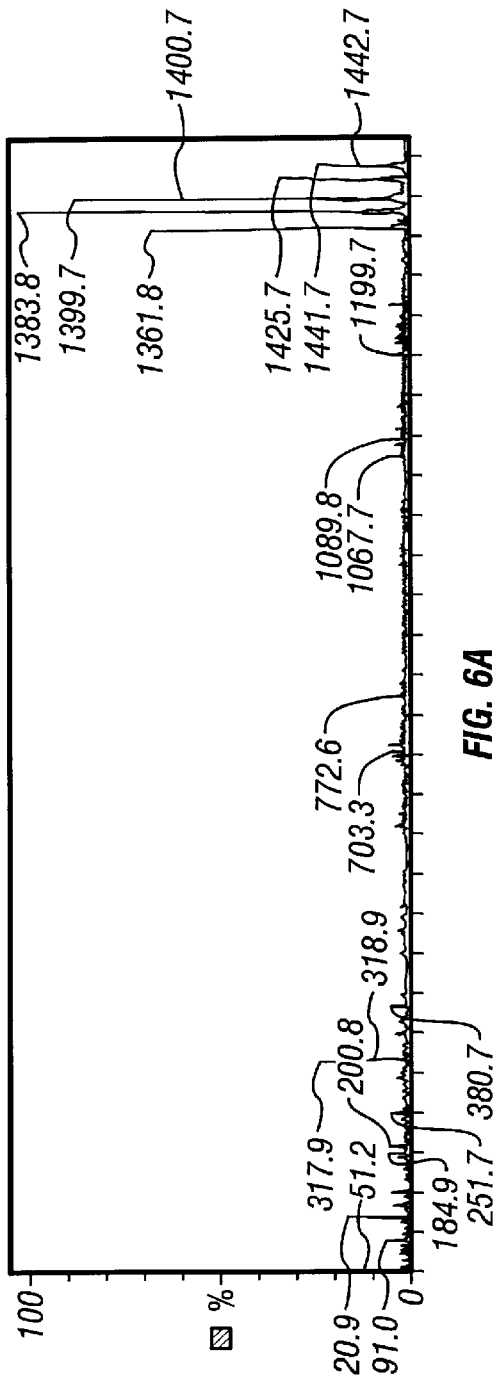
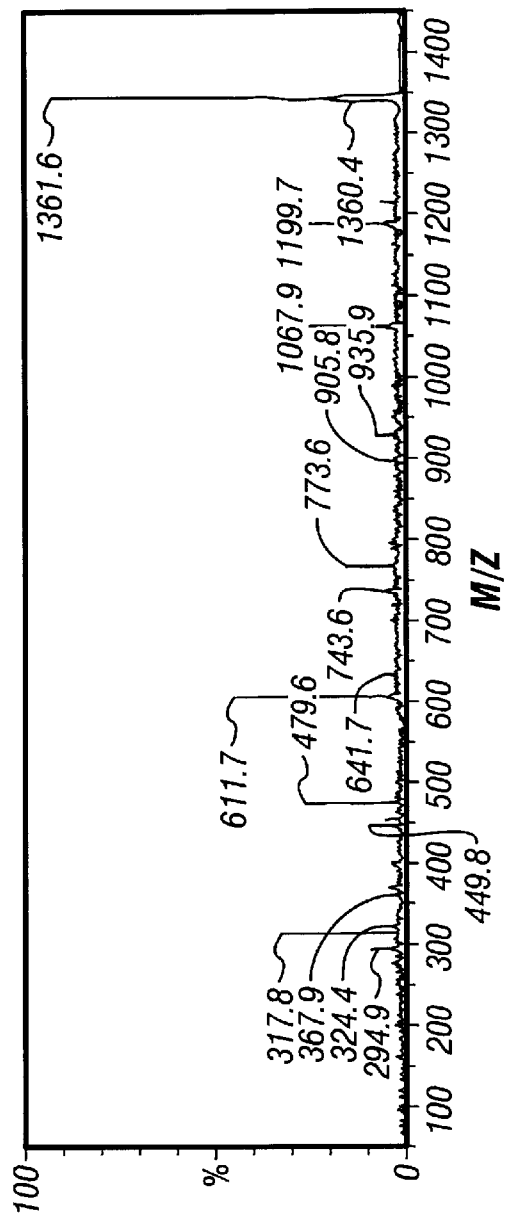
FIG. 6A
FIG. 6B

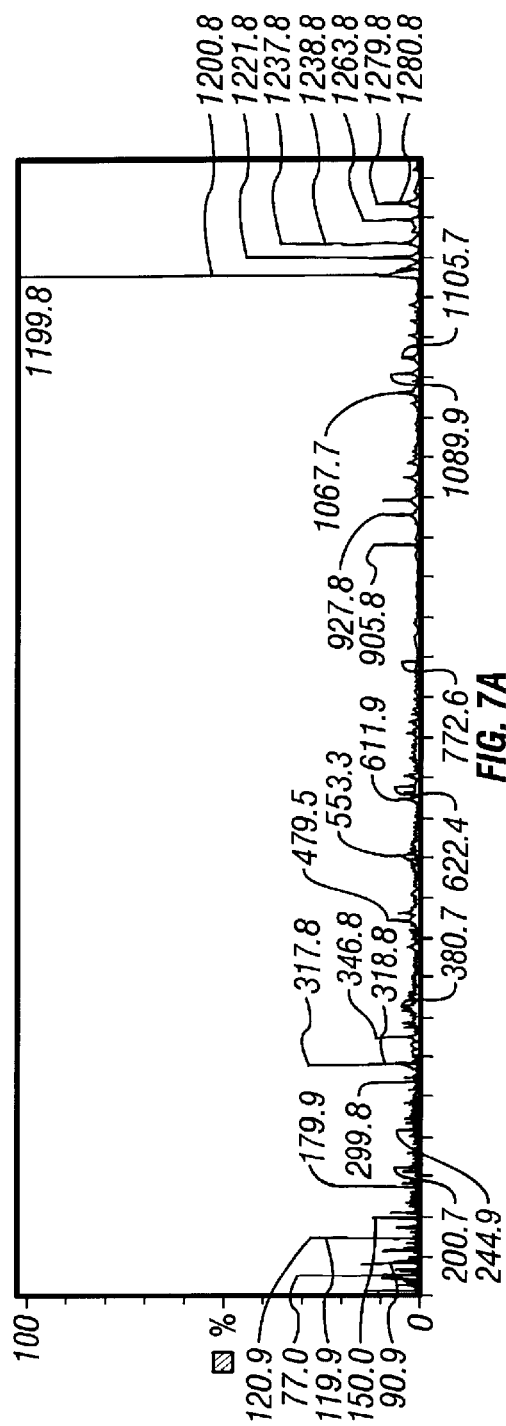
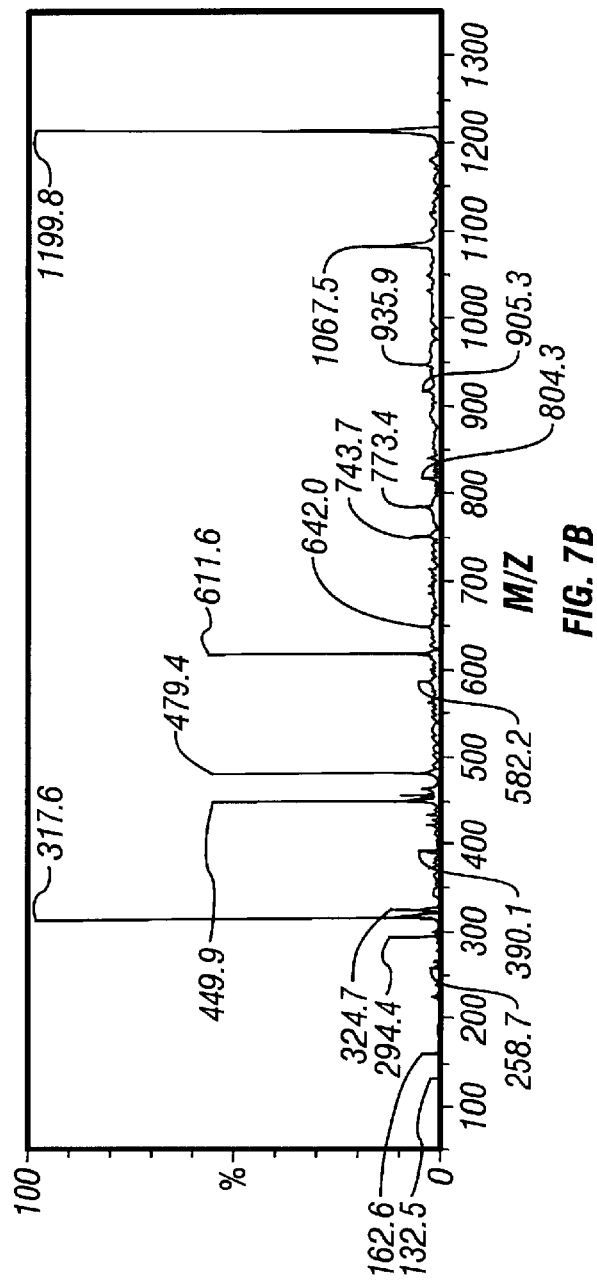
FIG. 7A
FIG. 7B

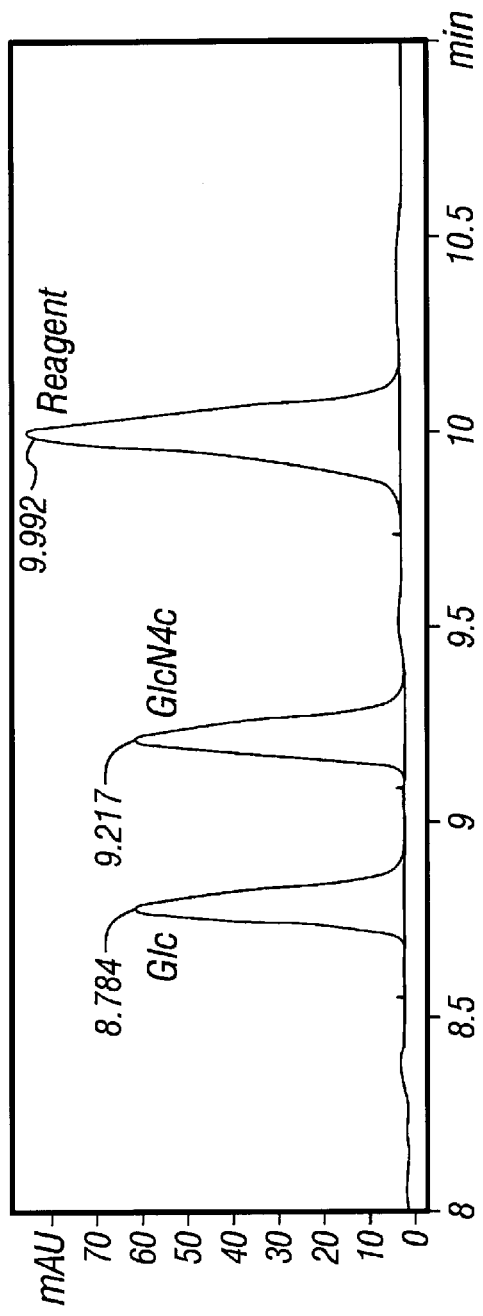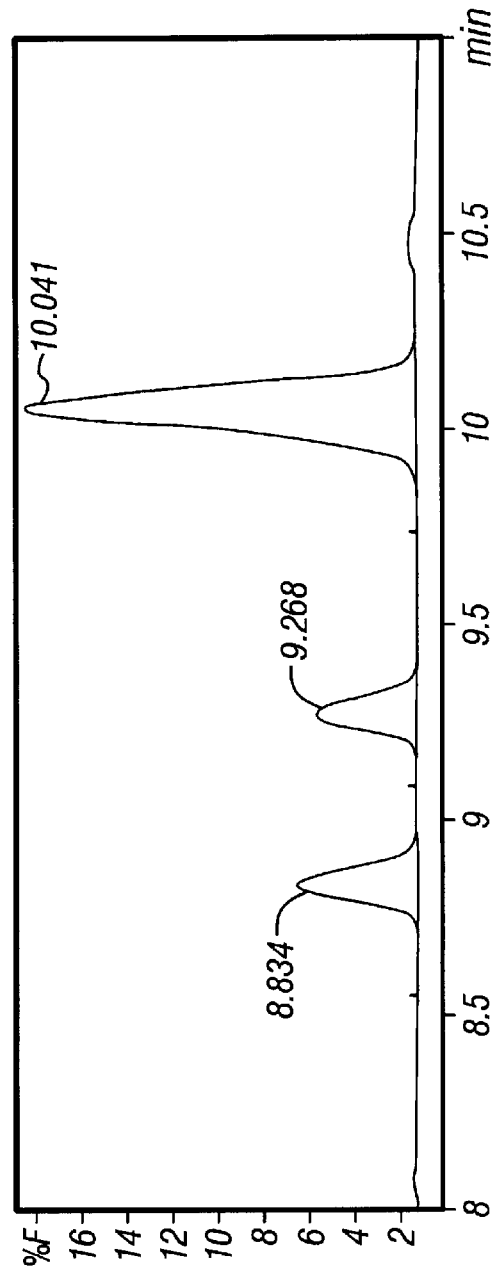
FIG. 8A
FIG. 8B

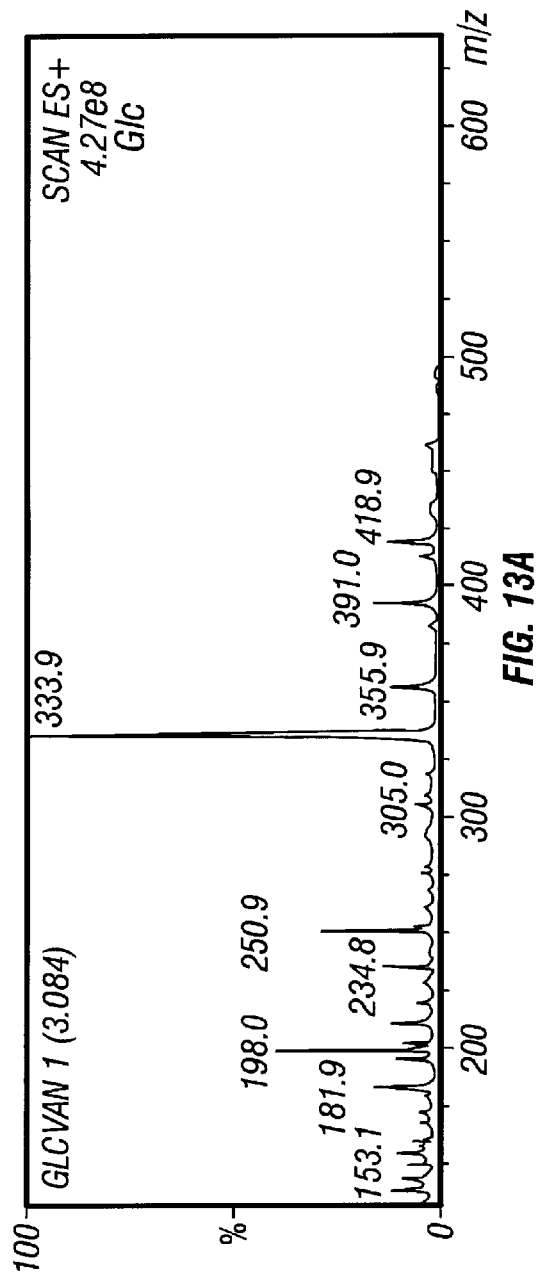
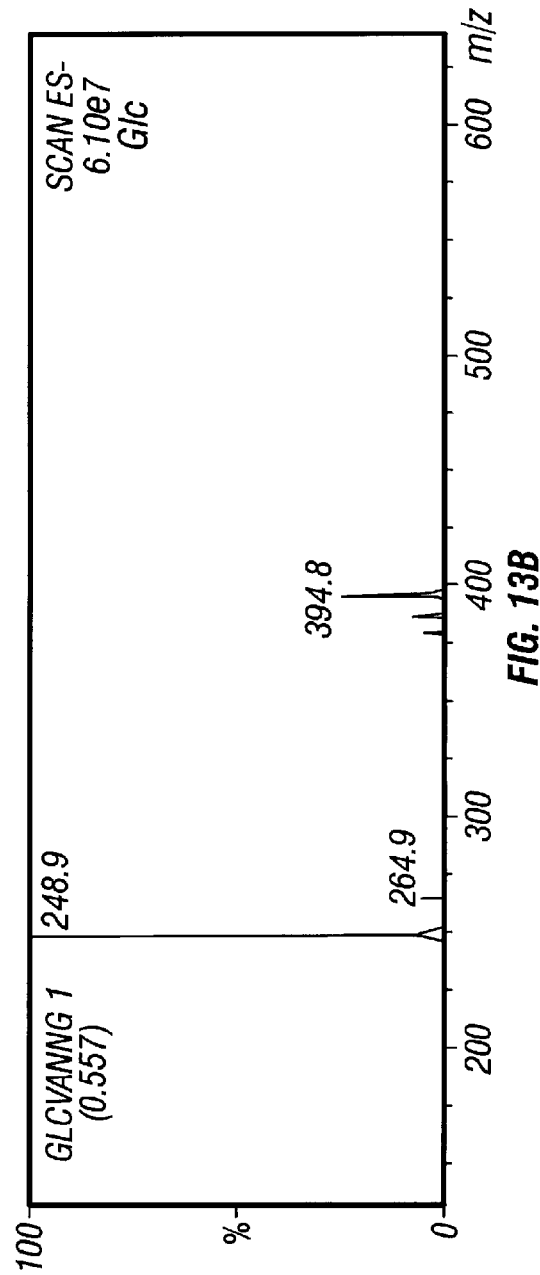
FIG. 13A
FIG. 13B

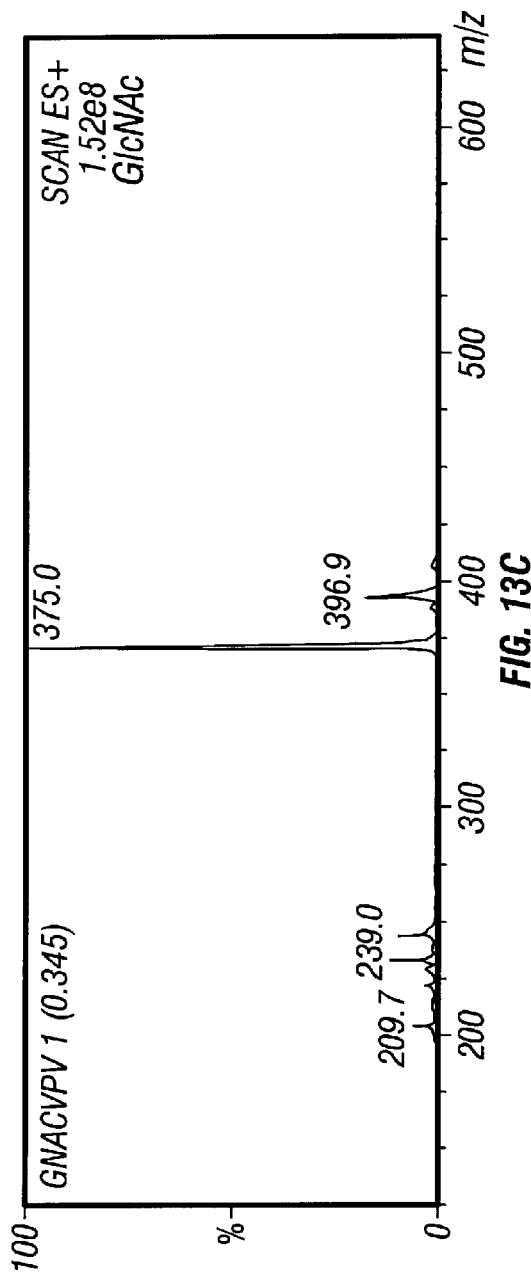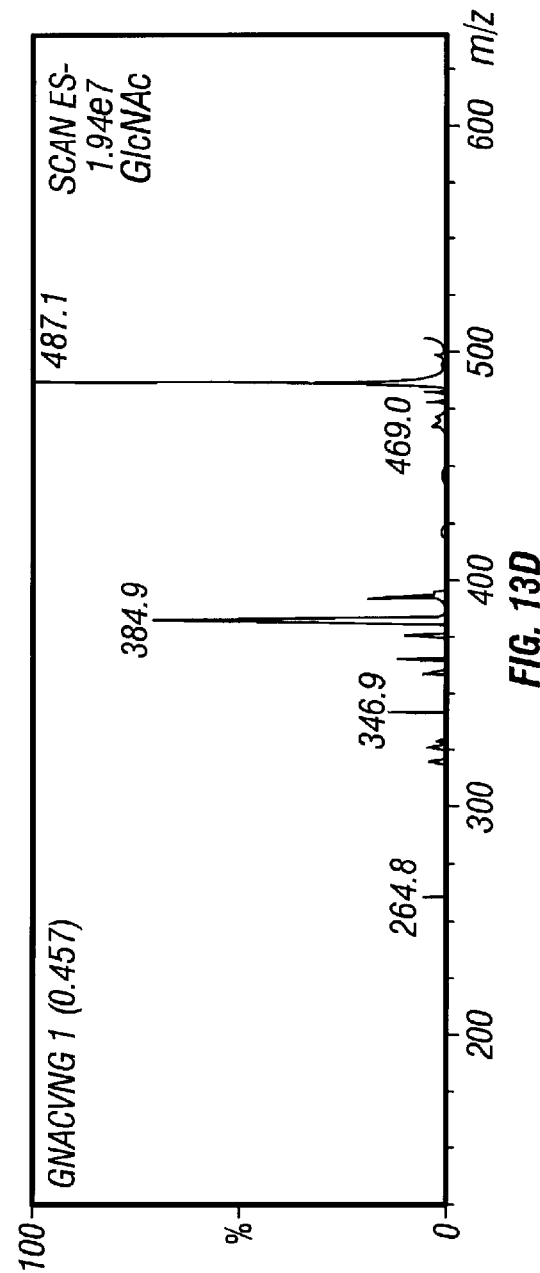

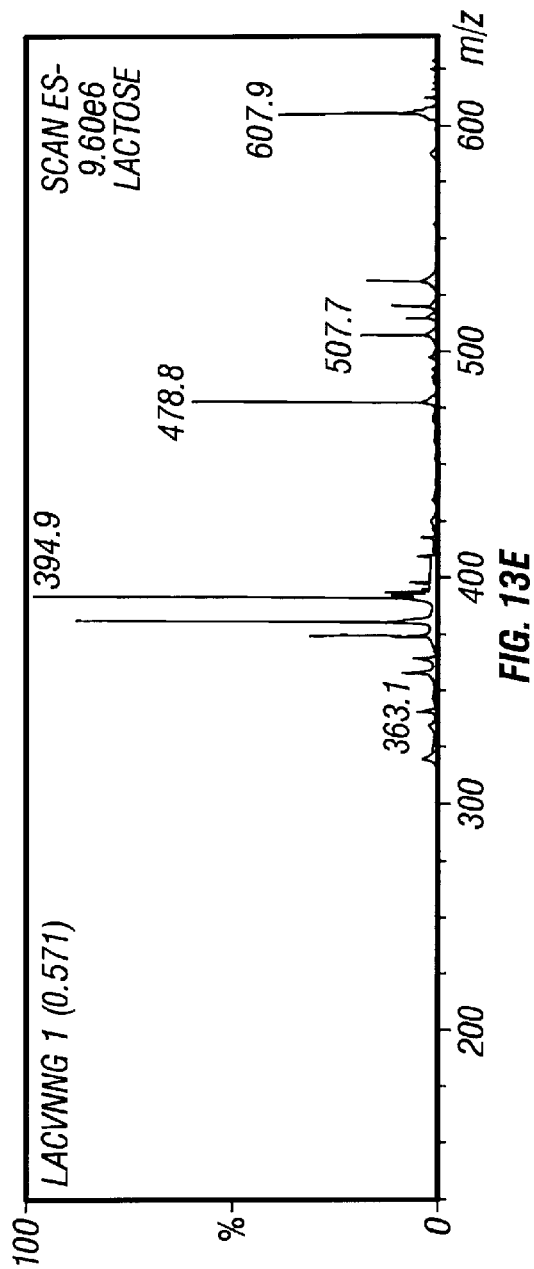
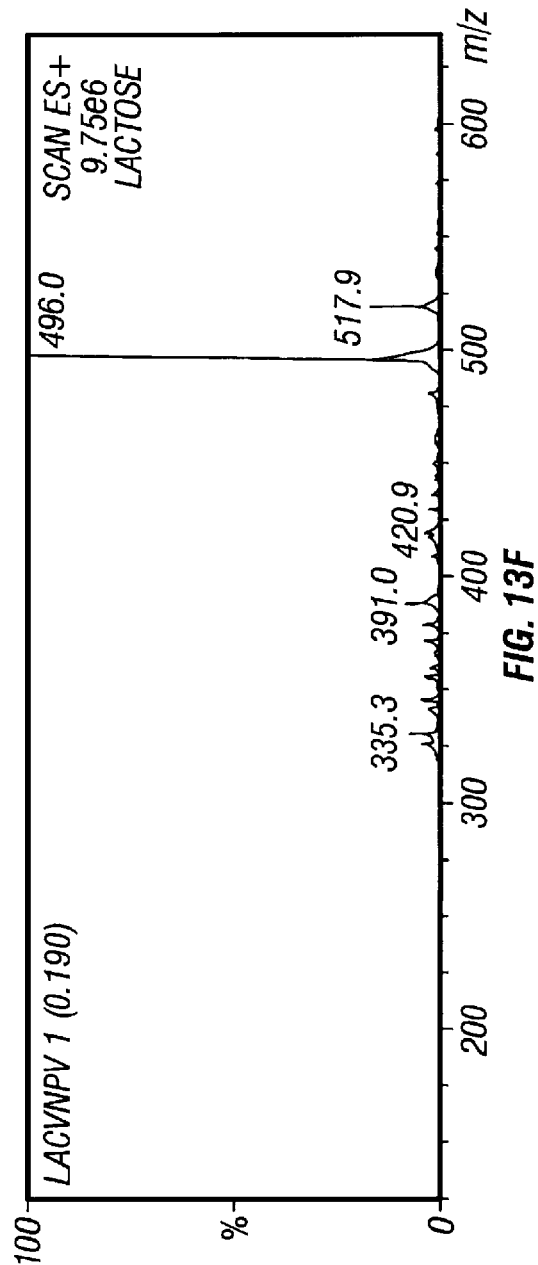
FIG. 13E
FIG. 13F

GLYCAN DERIVATIVES

TECHNICAL FIELD

The invention relates to methods to produce glycan derivatives and particularly to hydroxylamination of glycans.

BACKGROUND ART

As interest in the biological role of complex sugars (glycans) develops, it has become increasingly important to have improved methods for the separation and analysis of glycans. A primary problem in the analysis of glycans is the difficulty in detection of the small amounts which are typically available (at the picomol level or less). To this end, methods have become available which employ either radiochemical labelling of the glycans, or the attachment of UV-absorbing or fluorescent labels.

Radiochemical labels are usually introduced by reduction with tritium-labelled borohydride. This approach suffers the disadvantages associated with the use of radioactive materials, but is rigorously quantitative in the sense that, when the reduction is carried to completion, there is a direct correspondence between the molar amounts of different glycan species present in a mixture and the relative amounts of tritium label incorporated.

To date, the standard method of introducing labels has been by reductive amination (RA. FIG. 1), whereby the glycan is converted by an excess of a primary aromatic amine into an acyclic imine, which is stabilised by reduction with cyanoborohydride. This is achieved by heating in an acidic medium, often in the presence of an organic co-solvent, such as dimethyl sulfoxide. The presence of the acid as a catalyst for the derivatisation has a potentially serious disadvantage that it can effect the hydrolysis of labile linkages in the glycans, particularly those of sialic (neuraminic) acids. Moreover, the quantitative aspects of reductive amination of glycans are rather problematic [Suzuki et al. 1992; Evangelista et al. 1996], with considerable potential for the distortion of the quantitative results.

The persistence of problems in the RA of glycans underlines the lack of fundamental understanding of the steps in the overall process, and the lack of appreciation of why it is so slow, where the rate-limiting steps lie and what competing reactions limit the quantitative outcomes. The overall reaction scheme is shown in FIG. 1. In principle, the rate of the overall process could be limited by:

i. the rate of opening of the terminal ring of the reducing glycan (equilibrium 1);

ii. the rate of condensation of the primary amine to form an imine (equilibrium 2);

iii. the rate and equilibrium distribution in the isomerisation to ring forms of the imine (equilibrium 3); or iv. the rate of reduction of the acyclic imine (step 4).

Each of these steps is subject to acid catalysis, and the improvement in rate in the presence of acid [Evangelista et al. 1996] is not in itself surprising. The degree of acidity required for effective reductive amination of sugars is, however, much greater than that required for simple aldehydes (which have steps 2 and 4 in common with the reaction of the sugar), suggesting that the acid catalysis is required for step 1 or step 3.

Glycan nitrones have been prepared from O-protected D-arabinose derivatives (Paulsen and Budzis, 1974), but not from non-protected monosaccharides and glycans, such as described in this document. The examples of particular relevance have nitrones formed by condensation of the free reducing terminus (the pro-aldehyde at C1) with an N-substituted hydroxylamine. In all such cases, the nitrone product was determined to exist in an open-chained (acyclic) form, on the basis of proton nuclear magnetic resonance (nmr) properties. In this earlier study (Paulsen and Budzis, 1974), the reported nitrones were not submitted to reduction.

For the effective analysis of glycans, including those with acid-labile linkages, it is desirable to have a method which can replace that of reductive amination of primary aromatic amines, and which does not require the inclusion of large amounts of acid to the reaction mixture. The present inventors have developed a new method for producing derivatives of glycans which employs reaction of reducing glycans with mono-N-substituted hydroxylamines, which condense with the glycans to form glycan nitrones which are readily reduced to the stable products. N,N-disubstituted hydroxylamines. The advantage of this method is that the overall reaction can be performed at pH 6 or above, and is so rapid that aldoses can be completely derivatised without necessarily heating for long periods.

DISCLOSURE OF INVENTION

In a first aspect, the present invention consists in a method of producing a glycan nitrone comprising reacting the glycan with a mono-N-substituted hydroxylamine at pH 6 or greater to form a glycan nitrone.

In a preferred embodiment of the first aspect of the present invention, the reaction is carried out at pH 6.5 or above.

Mono-N-substituted hydroxylamines suitable for use in the first aspect of the present invention include benzylic N-substituted hydroxylamines and N-arylhydroxylamines.

Benzylic N-substituted hydroxylamines can readily be prepared by reduction of oximes obtained by reaction of aromatic aldehydes with hydroxylamine. In particular, N-(3-methoxylbenzyl)hydroxylamine and N-(3,4-methylenedioxybenzyl)hydroxylamine can be prepared from 3-methoxybenzaldehyde and piperonal, respectively. Benzylic N-substituted hydroxylamines can also be prepared by alkylation of hydroxylamine using an excess of a benzyl halide, with formation of an N,N-disubstituted hydroxylamine, from which one of the aralkyl substituents is removed by mild oxidation followed by hydrolysis.

N-arylhydroxylamines are most conveniently prepared by reduction of corresponding nitro compounds or oxidation of the corresponding primary amines. The success of this approach has been demonstrated by reduction of nitrobenzene to N-phenylhydroxylamine. Alternatively, N-arylhydroxylamines can be prepared by oxidation of the corresponding amines, for instance by using samarium diiodide as oxidant.

In a second aspect, the present invention consists in a method of producing a glycan derivative comprising reacting a glycan nitrone with a reducing agent to form a hydroxylamine glycan derivative.

Preferably, the glycan nitrone is produced by the method according to the first aspect of the present invention.

A reducing agent suitable for this reaction is sodium cyanoborohydride. It will be appreciated, however, that other reducing agents would also be suitable for use in this method.

The method of the present invention allows the inclusion of detectable labels on glycans that are useful in a number of separation and analytical procedures. Furthermore, the glycan derivatives produced by the methods of the present invention can have active moieties introduced therein that are useful for attaching glycans to supports.

The glycan derivatives of the present invention, whether in the form of nitrone or hydroxylamine derivatives, are particularly useful for the analysis or solid-phase immobilisation of glycans and sugars.

The methods of the present invention are also useful for the derivatisation of any carbonyl compound obtained from a glycan or glycoconjugate by any chemical treatment, such as by periodate oxidation or deamination using nitrous acid, or enzymic treatment, such as by treatment with galactose oxidase. Furthermore, the methods of the present invention can be used for the derivatisation of any carbonyl compound obtained from any compound of biological or environmental interest for the purposes of enhancing its separation, purification or detection properties.

The methods of the present invention are particularly useful as a means of attaching to a monosaccharide or glycan a label which confers ultraviolet-absorbing or fluorescent properties which enhance its detection properties, or any other groups which enhance the detection of the monosaccharide or glycan by application of enzymic, chemical or physical reagent or method.

The methods of the present invention are useful as a means of attaching to a monosaccharide or glycan a label which confers modified or improved properties for separation by any method of chromatography, electrophoresis, attachment to a solid support, phase extraction or any other physical, chemical or biological method.

The methods of the present invention are useful as a means of attaching to a monosaccharide or glycan a label which confers modified or improved properties for analysis by any form of mass spectrometry.

A glycan, or a glycoconjugate in which one or more carbonyl groups have been introduced by chemical or enzymic treatment can also be derivatised according to the methods of the present invention.

The methods of the present invention can be used for derivatisation of a reducing glycan, or any modified glycan into which one or more carbonyl groups have been introduced by chemical or enzymic treatment, using reduction at a pH of 6 or above.

A glycan which has been immobilised on a solid support, either as a nitrone, or as a hydroxylamine derivative obtained by reduction of a nitrone, can be used for probing by antibodies, lectins or other reagents, or for the purpose of degradation or any other form of chemical or enzymic modification. Such glycan derivatives can also be used for the purposes of carrying out any form of affinity fractionation or purification of a protein, glycoprotein, glycan or any other biological or biologically-active substance.

The methods of the present invention can be used to label a cell-surface glycan or glycoconjugate, or a cell-surface glycan or glycoconjugate which has been modified either chemically, such as by oxidation by periodate, or enzymically, such as by galactose oxidase, for the purpose of identifying, separating or analysing glycan or glycoconjugate components which are located at the surface of a cell or cells.

The methods of the present invention can be used to label any other cell-surface component, including such components which have been modified by any enzymic or chemical method in order to incorporate an aldehyde or ketone group, for the purpose of identifying, separating or analysing those components which are located at the surface of a cell or cells.

As used herein, the term 'glycan' refers to a monosaccharide, oligosaccharide or polysaccharide containing one or more different monosaccharide subunits. Unless stated otherwise, 'glycan' refers to an unprotected glycan.

In order that the present invention may be more clearly understood, preferred forms will be described with reference to the following examples and drawings.

BRIEF DESCRIPTION OF THE DRAWINGS

FIGS. 5A and B show mass spectra of DP 9 xyloglucan subunit;

FIGS. 6A and B show mass spectra of DP 8 xyloglycan subunit;

FIGS. 7A and B show mass spectra of DP 7 xyloglycan subunit;

FIGS. 8A and B are chromatograms showing the HPLC separation of N-[3-methoxybenzyl]hydroxylamine derivatives produced from glucose and N-acetylglucosamine with an excess of derivatisation reagent;

FIGS. 13A–13F show results of electrospray mass spectrometry positive and negative ion ESI/MS of the N-(4-hydroxy-3-methoxybenzyl) hydroxylamine derivatives of glucose, N-acetylglucosamine and lactose;

MODES FOR CARRYING OUT THE INVENTION

Derivatisation of Glycans by Reductive Hydroxylamination (RHA)

Figure 2:
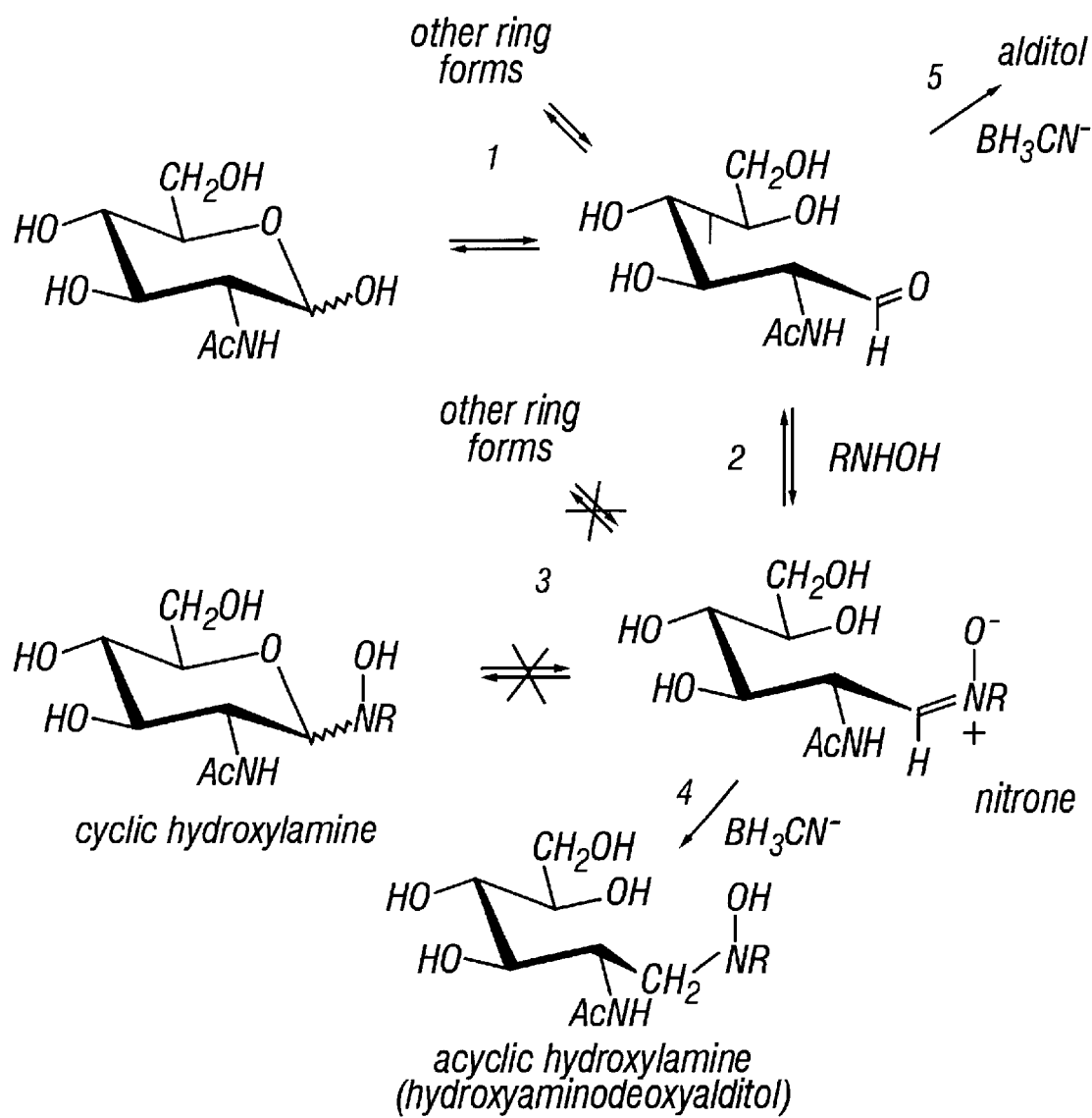
FIG. 2 shows the chemical reaction of reductive hydroxylamination of glycans according to the present invention, using N-acteylglucosamine as an example.

When glucose or N-acetylglucosamine is treated with N-substituted hydroxylamine in the absence of reducing agent, a significant yield of the nitrone is obtained, with the formation of a turbid solution, presumably because of the limited solubility of the nitrone. If a co-solvent such as ethanol is added to maintain the product in solution, however, only trace amounts of the nitrone are obtained. The present inventors conclude from this observation that:

i. the ring opening of the sugar (FIG. 2 equilibrium 1, the essential first step before reaction) is rapid;
ii. that the establishment of an equilibrium, between the sugar and the N-substituted hydroxylamine as reactants and the nitrone as intermediate (FIG. 2, step 2), is also rapid;
iii. the equilibrium does not favour formation of the nitrone.

The fact that a high degree of conversion occurs under conditions where the nitrone is not soluble shows, however, that the equilibrium is mobile, and that it shifts when the nitrone product is removed from the system.

Figure 1:
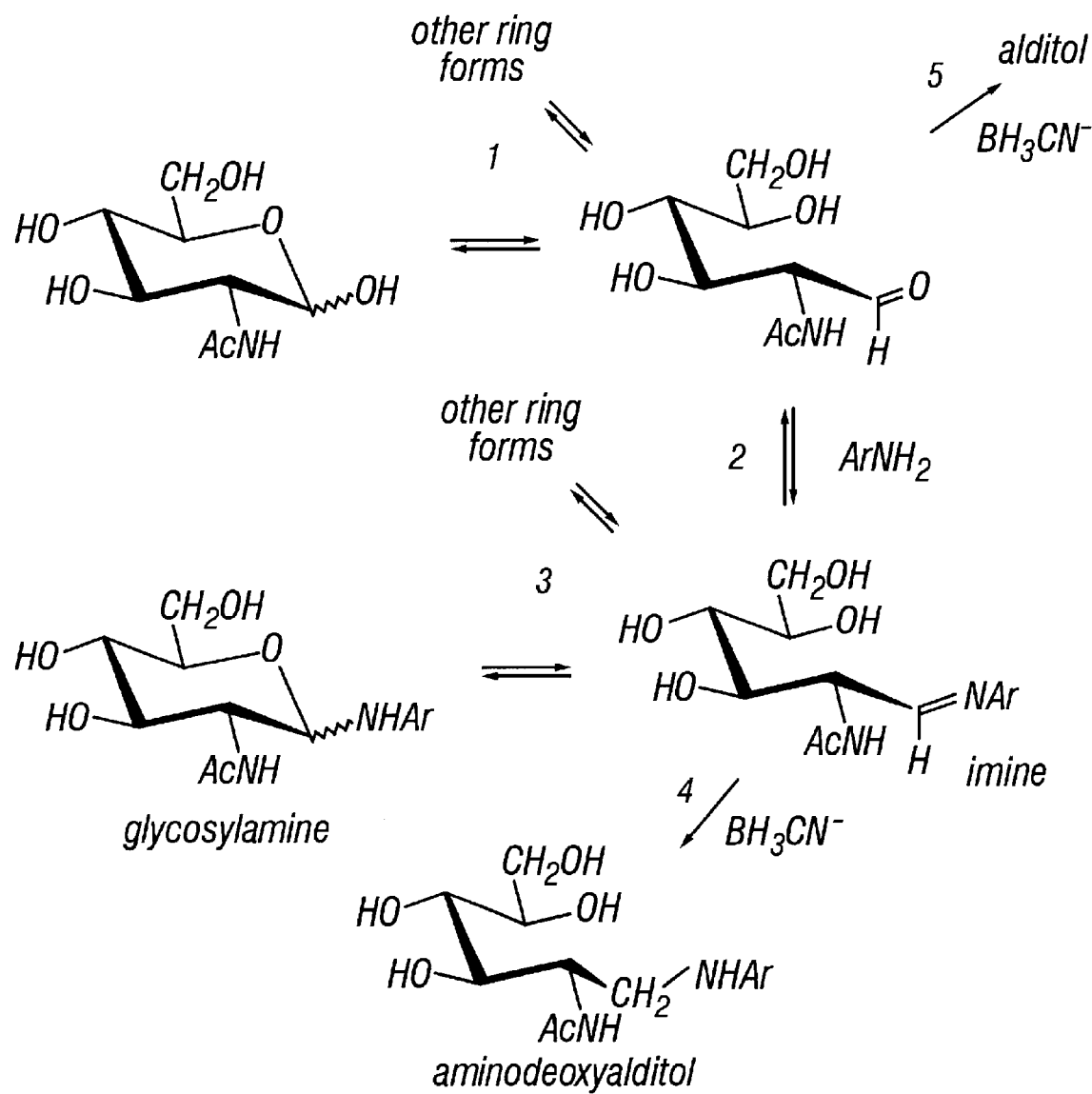
FIG. 1 shows the chemical reaction of reductive amination of glycans using N-acteylglucosamine as an example.

When cyanoborohydride is included in the reaction system, even in the presence of a co-solvent, the reduced products are formed rapidly, which is attributed to the removal of the nitrone (FIG. 2, step 4) from the equilibrium reaction. The reduction is very rapid in RHA compared to the reduction of the analogous imine intermediate in the RA procedure. This is attributed to a combination of an accelerated rate of reduction of the nitrone (due to the inherent charge separation) and to the fact that nitrones do not appear to exist as ring isomers (FIG. 2, equilibrium 3), which are resistant to reduction. Equilibrium 1, which is identical in FIGS. 1 and 2, cannot be the rate-limiting step in the slow RA.

Figure 10:
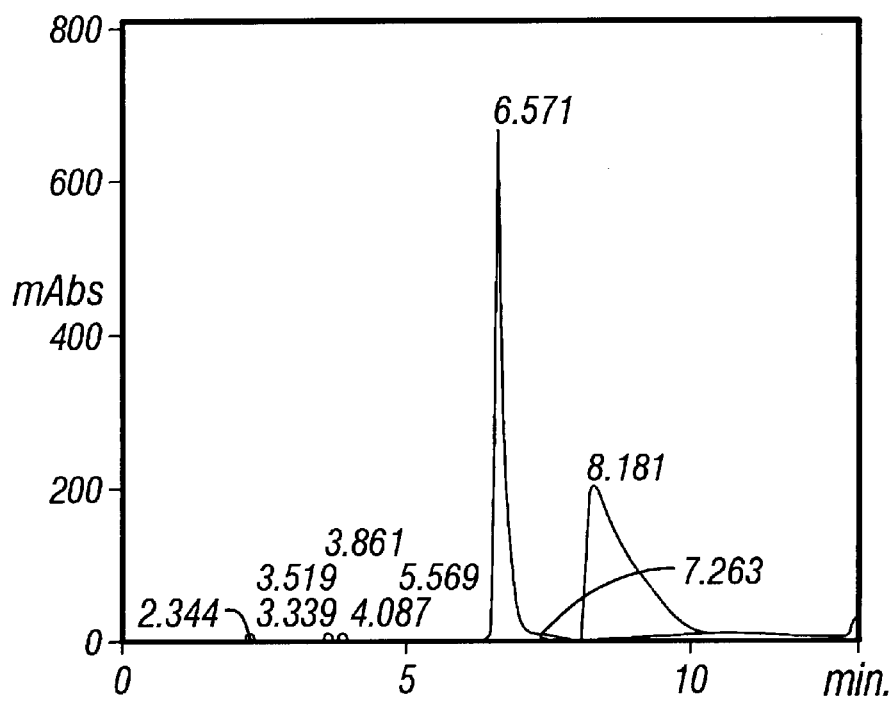
FIG. 10 is a chromatogram showing the HPLC separation of N-[3,4-methylenedioxybenzyl]hydroxylamine-labelled lactose.

In the light of differences in rates of reductive amination of different sugars, notably glucose and N-acetylglucosamine [Evangelista et al. 1996], it was anticipated that there would be similar differences in the rates of labelling by nitrone reduction. This was demonstrated in a competition experiment in which equimolar amounts of these two sugars were treated with a sub-equivalent amount of N-substituted hydroxylamine under reducing conditions. The yield of the glucose product was some four times as great as that of the N-acetylglucosamine (FIG. 10), indicating a four-fold greater rate of reaction.

Preparation of N-substituted Hydroxylamines

Benzylic N-substituted hydroxylamines required for RHA of glycans can readily be prepared by reduction of oximes obtained by reaction of benzaldehydes with hydroxylamine. This versatile method allows access to reagents with differing UV-absorbing and fluorescence properties, as well as labels with chemical properties suitable for further reaction to enhance detection or to permit immobilisation on solid supports. The success of this approach has been demonstrated by synthesis of (A) N-(3-methoxylbenzyl) hydroxylamine and (B) N-(3,4-methylenedioxybenzyl) hydroxylamine from 3-methoxybenzaldehyde and piperonal, respectively. Benzylic N-substituted hydroxylamines can also be prepared by alkylation of hydroxylamine using an excess of a benzyl halide, with formation of an N,N-disubstituted hydroxylamine, from which one of the aralkyl substituents is removed by mild oxidation followed by hydrolysis.

N-arylhydroxylamines are most conveniently prepared by reduction of corresponding nitro compounds or oxidation of the corresponding primary amines. The success of this approach has been demonstrated by reduction of nitrobenzene to N-phenylhydroxylamine (C). Alternatively, N-arylhydroxylamines can be prepared by oxidation of the corresponding amines, for instance by using samarium diiodide as oxidant [Kende & Mendoza, 1991]. This latter approach has great flexibility, in that it enables the adaptation of primary aromatic amines, such as those presently in use for RA of glycans, to the preparation of N-arylglycosylamines for use in the more effective RHA of the glycans.

EXAMPLES

Reversed-phase Separation of Oligosaccharide Derivatives

Figure 3:
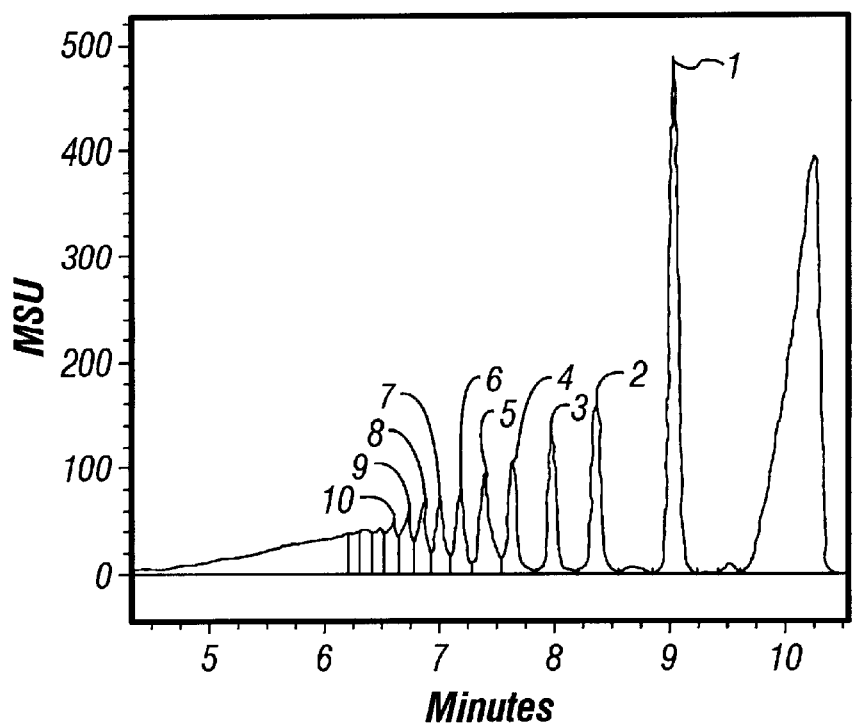
FIG. 3 is a chromatogram showing the HPLC separation of N-[3-methoxybenzyl]hydroxylamine derivatives produced from dextran.

1. N-(3-methoxybenzyl)hydroxylamine (MMBH)-dextrans. An acid hydrolysate of dextran, a glucose polymer, was treated with N-(3-methoxybenzyl)hydroxylamine at pH 6.5 and room temperature for 16 hours. The high-performance liquid chromatography separation (FIG. 3) was carried using an acetonitrile-water gradient on a reversed-phase column. Detection was by ultraviolet absorption at 275 nm. The numbers on the peaks (FIG. 3) correspond to the degree of polymerisation (the number of glucose units in each oligosaccharide).

Figure 4:
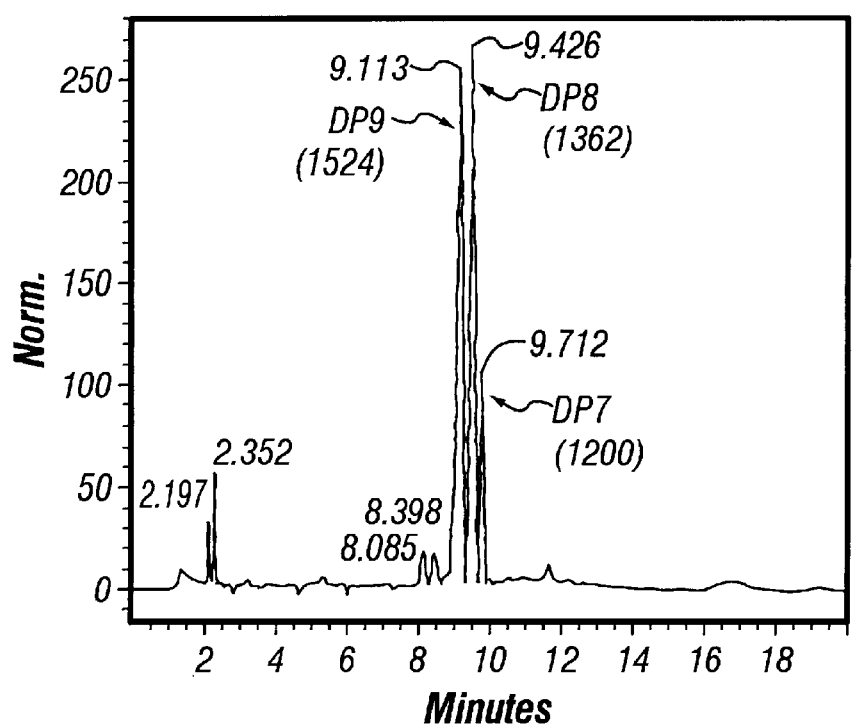
FIG. 4 is a chromatogram showing the HPLC separation of N-[3-methoxybenzyl]hydroxylamine derivatives produced from xyloglycan subunits with degree of polymerisation (DP) of 7, 8 and 9.

2. MMBH-xyloglucan fragments. Xyloglucan from tamarind was submitted to exhaustive treatment with *Aspergillus cellulase*, with the formation of the constituent oligosaccharide subunits of DP 7, 8 and 9. These were treated with N-(3-methoxybenzyl)hydroxylamine at pH 6.5 and room temperature for 16 hours and the derivatives separated by reversed-phase high-performance liquid chromatography (FIG. 4) as under 1 above. The peaks corresponding to the different subunits are labelled with the DP and with the mass of the protonated molecular ion obtained in electrospray mass spectrometry of the collected fractions. These mass spectra are shown in FIGS. 5A–5B, 6A–6B, and 7A–7B, corresponding to the oligosaccharides of DP 9, 8 and 7, respectively. In each figure, FIGS. 5A, 6A, and 7A correspond to the mass spectrum of the MMBH oligosaccharide, and shows that the protonated molecular (M+1) ion is obtained in good abundance. FIGS. 5B, 6B, and 7B correspond to collision-induced dissociation (CID) of the M+1 ion, and shows a series of daughter ions resulting from fragmentation of glycosidic bonds.

3. Derivatisation of an equimolar mixture of glucose and N-acetylglucosamine with excess N-(3-methoxybenzyl) hydroxylamine. Glucose, N-acetylglucosamine and N-(3-methoxybenzyl)hydroxylamine in the molar ratio of (1:1:4) were digested at pH 6.5 and room temperature for 40 hours in the presence of excess sodium cyanoborohydride. The product mixture was analysed by reversed-phase high-performance liquid chromatography (FIGS. 8A and 8B) with detection by absorbance at 275 nm (FIG. 8) and fluorescence (excitation at 275 nm, emission at 307 nm, FIG. 8B). FIG. 8A demonstrates the equal molar yield from each monosaccharide, while FIG. 8B demonstrates that the solvent composition influences the fluorescence quantum yield, and therefore the sensitivity of detection.

Figure 9:
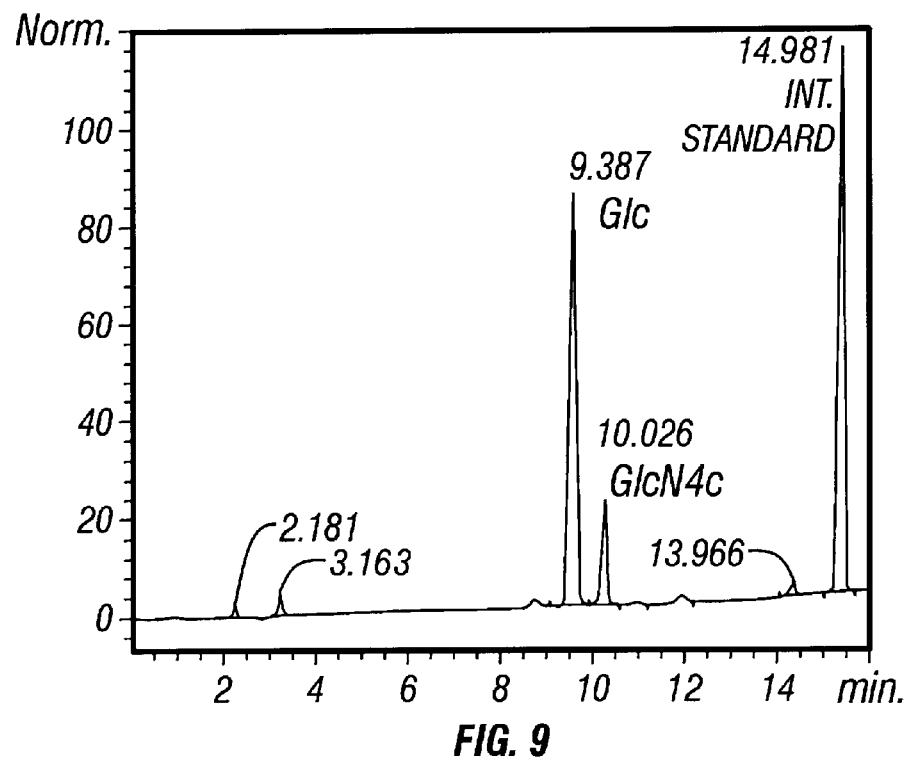
FIG. 9 is a chromatogram showing the HPLC separation of N-[3-methoxybenzyl]hydroxylamine derivatives produced from glucose and N-acetylglucosamine. The experiment was conducted as a competition assay with a limiting amount of derivatisation reagent, 2-phenoxyethanol was added as internal standard for quantitation.

4. Competition experiment: Derivatisation of an equimolar mixture of glucose and N-acetylglucosamine in the presence of a limited amount of N-(3-methoxybenzyl) hydroxylamine in the presence of a limited amount of N-(3-methoxybenzyl)hydroxylamine. Glucose, N-acetylglucosamine, N-(3-methoxybenzyl)hydroxylamine and 2-phenoxyethanol (internal standard) in the molar ratio of (10:10:2:2) were reacted at pH 6.5 and room temperature for 16 hours in the presence of excess sodium cyanoborohydride. The product mixture was analysed by reversed-phase high-performance liquid chromatography (FIG. 9) with detection by absorbance at 275 nm. The area of the glucose derivative is some 4 times that of the N-acetylglucosamine derivative, demonstrating a four-fold difference in the rates of derivatisation.

5. N-(3,4-methylenedioxybenzyl)hydroxylamine (MMDBH)-labelled lactose. The peak at 6.57 minutes (FIG. 10) corresponds to the lactose derivative, the reagent elutes at 8.18 minutes. Conditions used were an Alltech Alltima C18 20×4.6 mm column, eluted isocratically with 0.1% TFA/8% acetonitrile at 1 mL/min. Detection was at 288 nm.

Figure 11A:
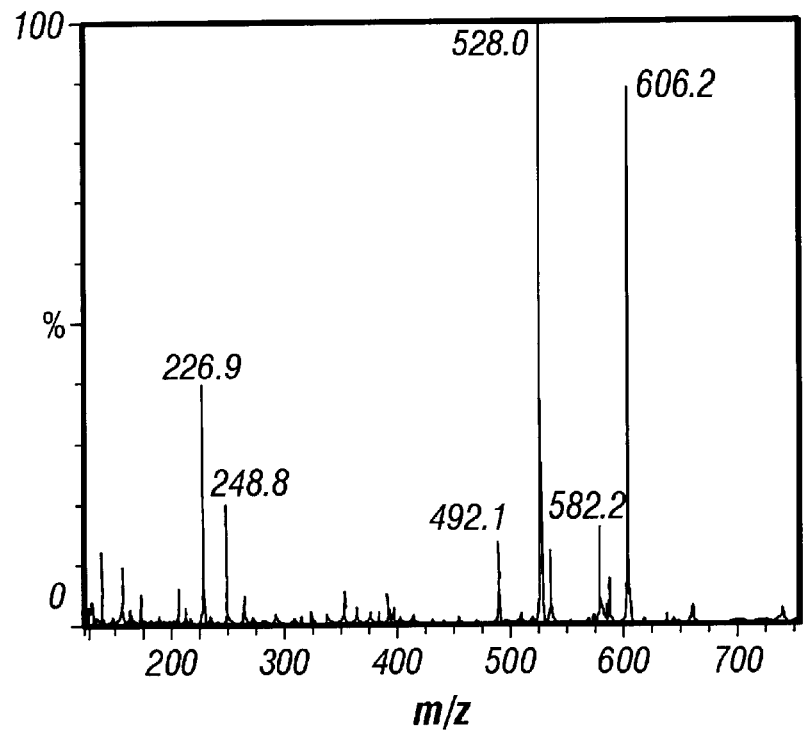
FIGS. 11A and B show results of electrospray mass spectrometry negative ion spectrum and positive ions spectrum of the lactose N-[3,4-methylenedioxybenzyl] hydroxylamine derivative, respectively.
Figure 11B:
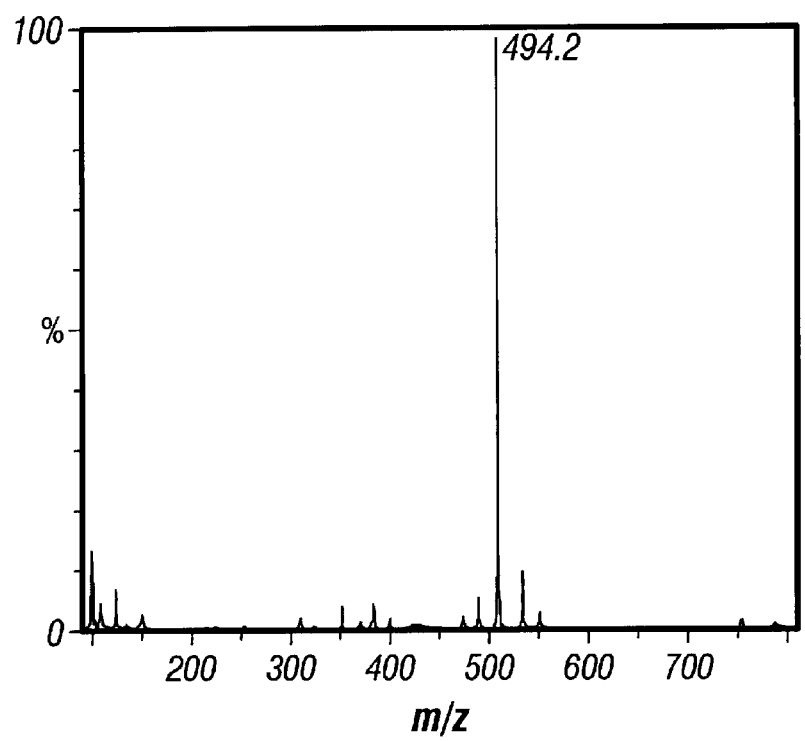

6. Electrospray mass Spectrometry
   a) Positive ion ESI/MS of the lactose N-3,4-methylenedioxybenzylhydroxylamine derivative (FIG. 11A, molecular weight 493) acquired following collection of the fraction eluting at 6.57 minutes in FIG. 10. The pseudomolecular ion is evident at 494 amu.
   b) Negative ion ESI/MS of the lactose 3,4-methylenedioxybenzyl derivative (FIG. 11B) acquired following collection of the fraction eluting at 6.57 minutes in FIG. 10. The trifluoroacetyl adduct is the major ion at m/z 606 (M+113) and a smaller ion at m/z 492 (M−H) is visible.

7. Reversed phase separation of the N-(3,4-methylenedioxybenzyl) hydroxylamine derivatives of galactose, glucose and mannose. The chromatograms are arranged in order of decreasing amounts of the monosaccharides used for derivatisation. The identity of the peaks are, with reference to FIG. 12A; galactose is the peak at 20.52 minutes, glucose is the peak at 21.77 minutes and mannose elutes at 23.14 minutes. The beginning of the N-3,4-methylenedioxybenzylhydroxylamine reagent peak can be seen at the end of the chromatogram. The column used was an Alltech Alltima C18, 250×4.6 mm. It was eluted with 0.2 M acetic acid pH 6 buffer. 10% acetonitrile for 18 minutes initially followed by a gradient to 70% acetonitrile over 8 minutes. Detection was at 288 nm and 10 mL was injected from a total of 200 mL of reaction mixture.

Figure 12A:
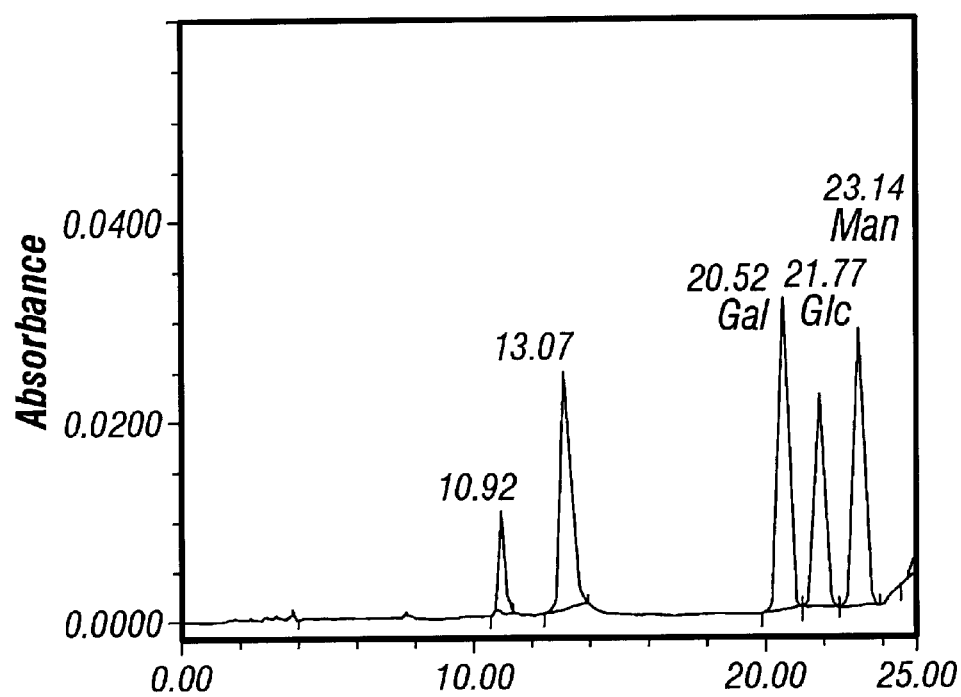
FIGS. 12–12C are a series of chromatograms showing the HPLC separation of N-[3,4-methylenedioxybenzyl] hydroxylamine derivatives of 2.5 nmoles, 250 pmoles and 25 pmoles of galactose, glucose and mannose, respectively.

FIG. 12A. This chromatogram corresponds to the injection of 2.5 nanomoles of each monosaccharide.

Figure 12B:
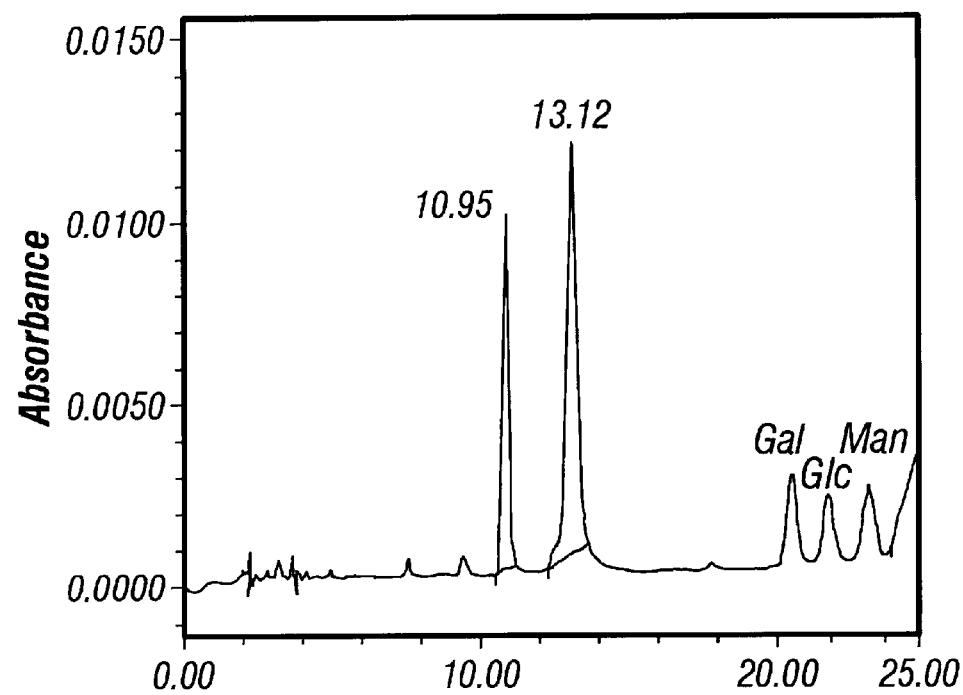

FIG. 12B. This chromatogram corresponds to the injection of 250 picomoles of each monosaccharide.

Figure 12C:
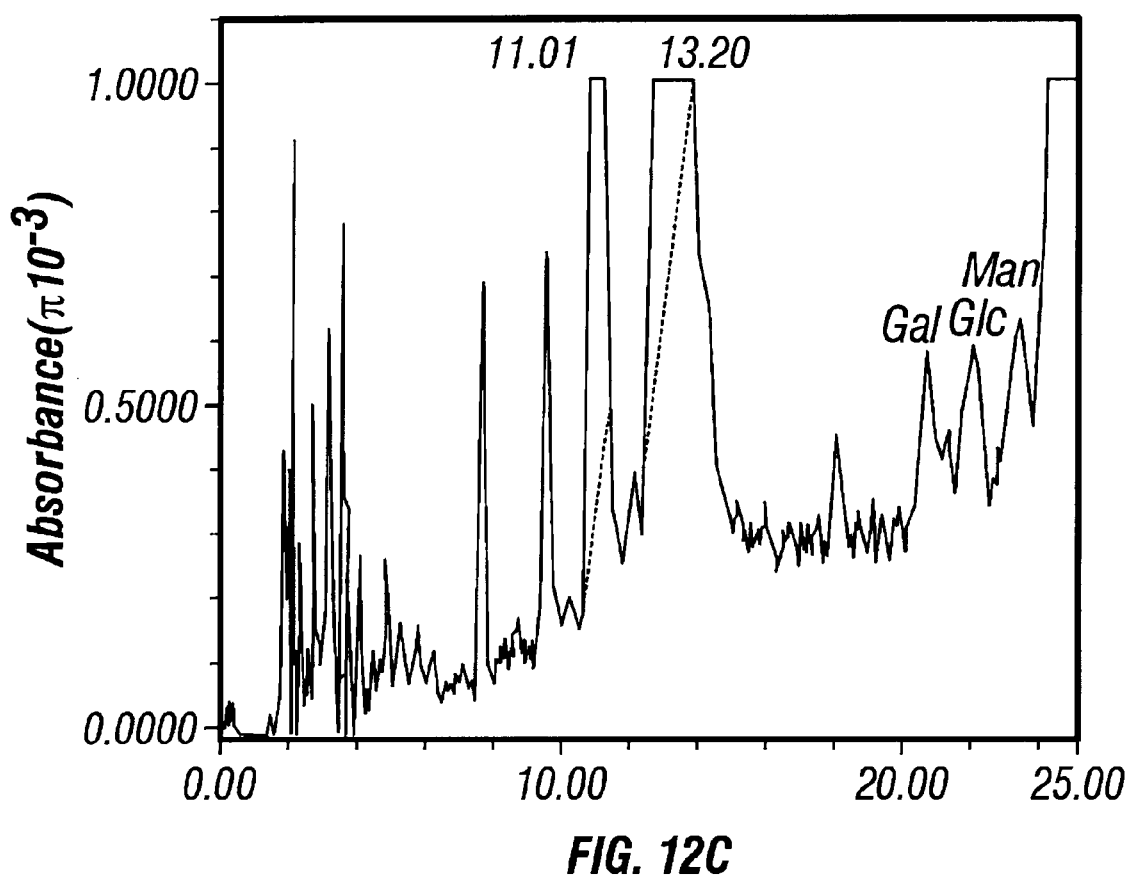

FIG. 12C. The detection limit of approximately 25 picomoles is evident from this chromatogram which corresponds to the injection of 25 picomoles of each monosaccharide.

8. Positive and negative ion ESI/MS of the N-(4-hydroxy-3-methoxybenzyl) hydroxylamine (HMBH) derivatives of glucose, N-acetylglucosamine and lactose. The spectra (FIGS. 13A–13F) correspond to (from the bottom of the page):

FIG. 13A. Positive ion spectra of the glucose derivative with mass 333 (M+H=333.9).

FIG. 13B. Negative ion spectra of the glucose derivative with mass 333.

FIG. 13C. Positive ion spectra of the N-acetylglucosamine derivative with mass 374 (M+H=375).

FIG. 13D. Negative ion spectra of the N-acetylglucosamine derivative indicating the trifluoroacetyl adduct at 487 m/z (M+113).

FIG. 13F. Positive ion spectra of the lactose derivative with mass 495 (M+H=496).

Figure 14:
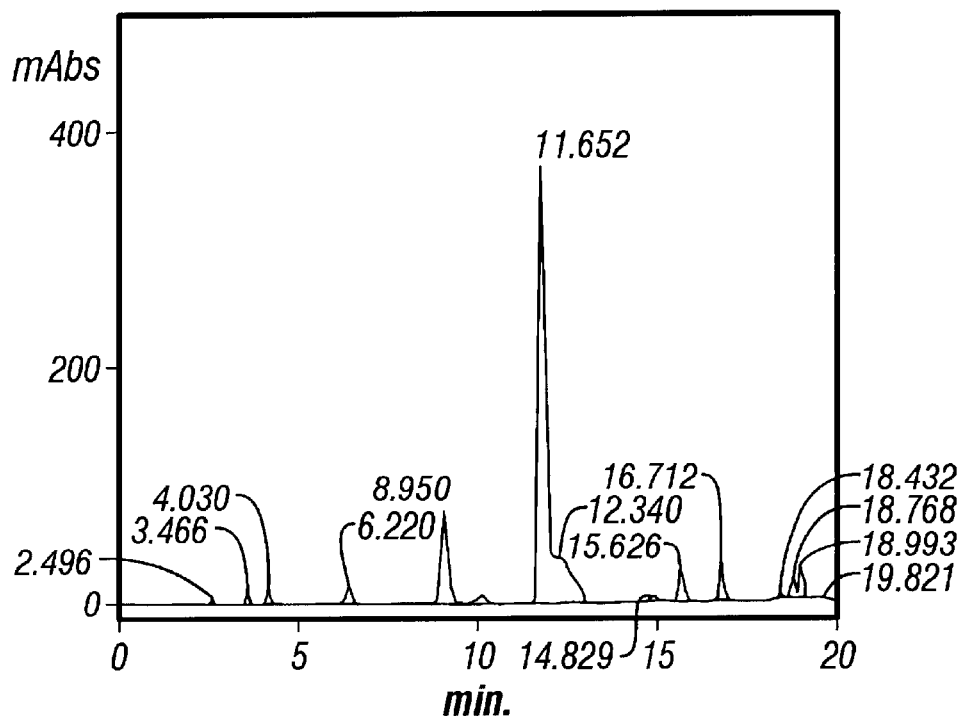
FIG. 14 is a chromatogram showing the HPLC separation of the N-phenylhydroxylamine derivative of lactose.

9. Reversed phase separation of the N-phenylhydroxylamine (PH)derivative of lactose. Conditions used were an Alltech Alltima C18 20×4.6 mm column, eluted isocratically with 0.1 % TFA/8% acetonitrile at 1 mL/min. Detection was at 274 nm. The peak at 8.95 minutes (FIG. 14) corresponds to the lactose N-phenylhydroxylamine derivative and the peak at 11.65 minutes is the reagent.

10. ESI/MS of the N-phenylhydroxylamine reagent and the N-phenylhydroxylamine lactose derivative. The lactose derivative was purified by collecting the peak at 8.95 minutes shown in FIG. 14.

Figure 15A:
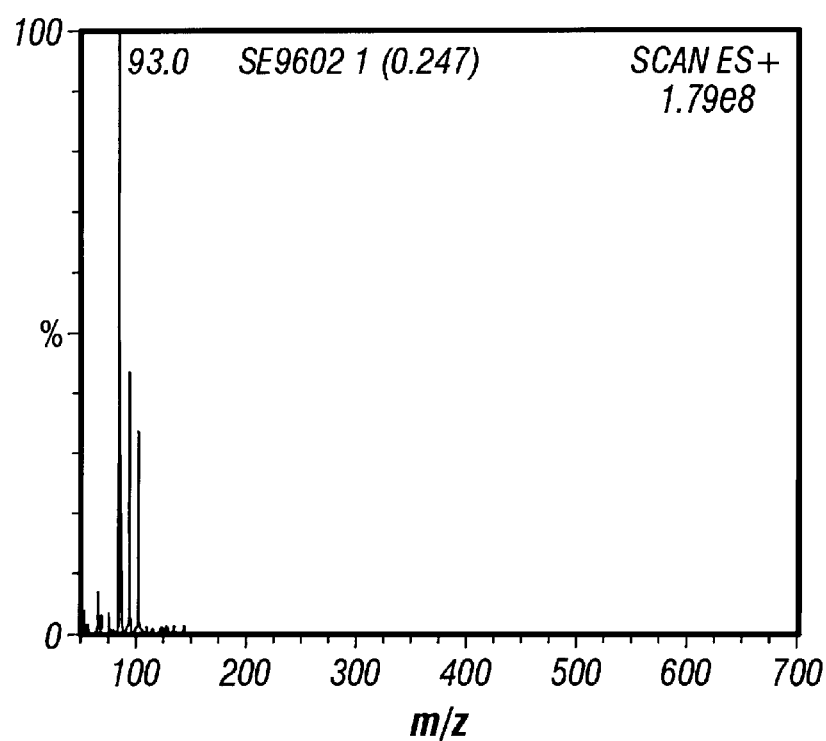
FIGS. 15A–15C show results of electrospray mass spectrometry positive ion ESI/MS of the N-phenylhydroxylamine reagent and the positive and negative ion ESI/MS of the N-phenylhydroxylamine lactose derivative.

FIG. 15A. Positive ion spectra of N-phenylhydroxylamine (mass 109).

Figure 15B:
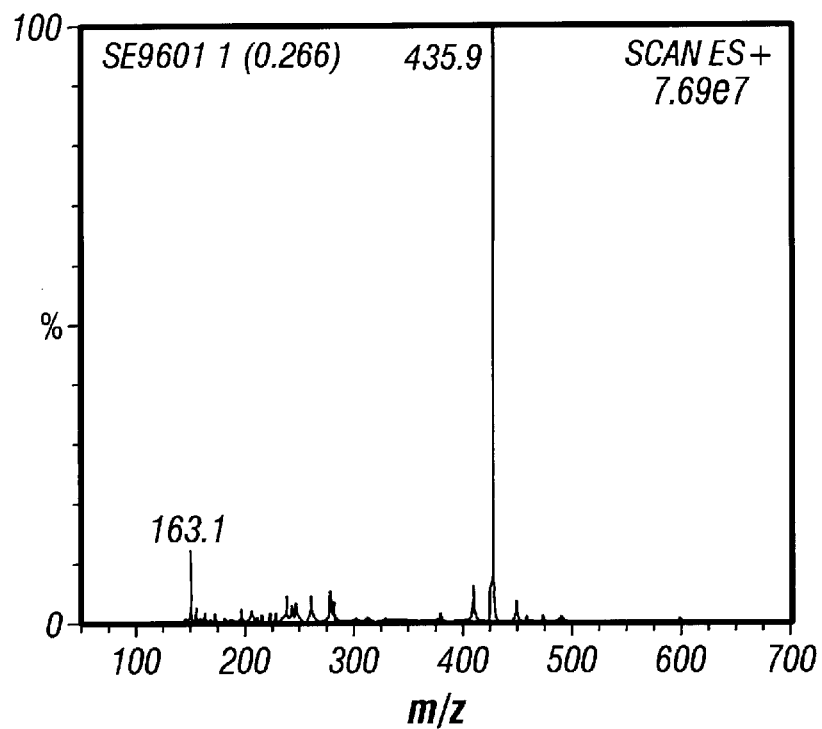

FIG. 15B. Positive ion spectra of the N-phenylhydroxylamine labelled lactose derivative. The pseudomolecular ion is evident at m/z 435.9.

Figure 15C:
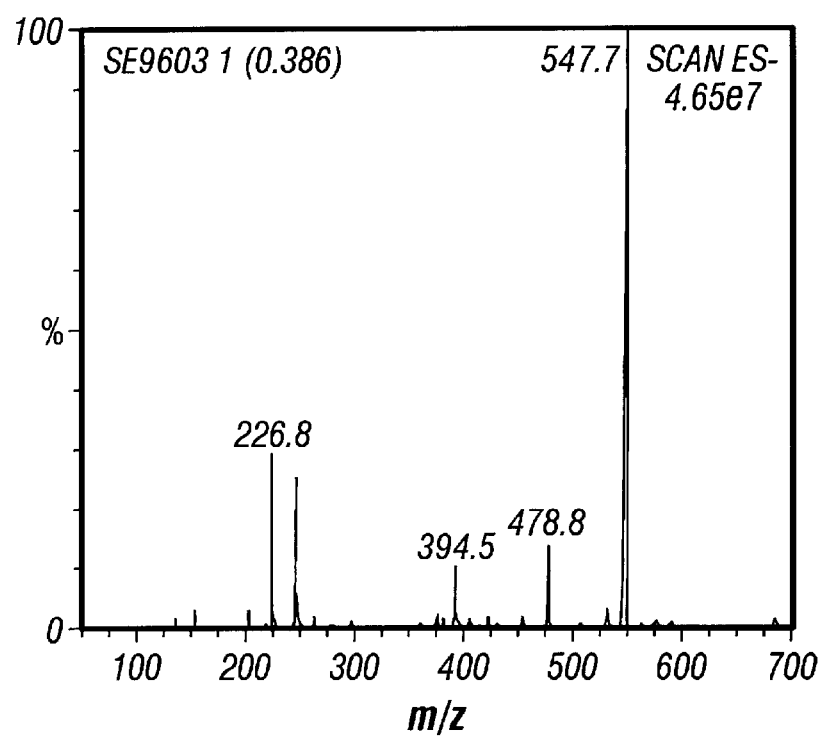

FIG. 15C. Negative ion spectra of the N-phenylhydroxylamine labelled lactose derivative. The trifluoroacetyl adduct is evident at 547.7 m/z (M+113).

One advantage of the method according to the present invention is that the overall reaction can be performed at pH 6 or above, and is so rapid that aldoses can be completely derivatised without heating for long periods.

11. Labelling reducing sugars with fluorescent hydroxylamine. Oligosaccharides from 1 mg of ovalbumin and fetuin were released using the PNGase F oligosaccharide release kit from Bio-Rad. After digestion each sample was applied to a 1 g carbograph solid phase extraction cartridge (Alltech Associates) and washed with 5 mL of water. The carbohydrates were then eluted with 5 mL of 25% acetronile/0.1% TFA and then lyophilised.

The lyophilised sample was resuspended in 100 $\mu$L of 0.1 M sodium phosphate buffer pH 7. Twenty $\mu$L of 0.1M (3,4-methylenedioxybenzyl)hydroxylamine and 20 $\mu$L or 0.2 M NaCNBH$_3$ in phosphate bugger pH 7 were added, the sample shaken and then heated at 50° C. for 16 hours before drying in a centrifugal evaporator. The sample was redissolved in 50 $\mu$L of 60% acetronile and 25 $\mu$L was injected into the HPLC. HPLC was performed using a GBC Aninomate HPLC (GBC Scientific, Victoria, Australia) This was comprised of a model LC-1150 quaternary pump, and model LC-1250 fluorescence detector interfaced to a PC running GBC Winchrom software. Eluents were degrased using an on-line solvent degasser. Samples were injected using a Rheodyne injector.

Figure 16:
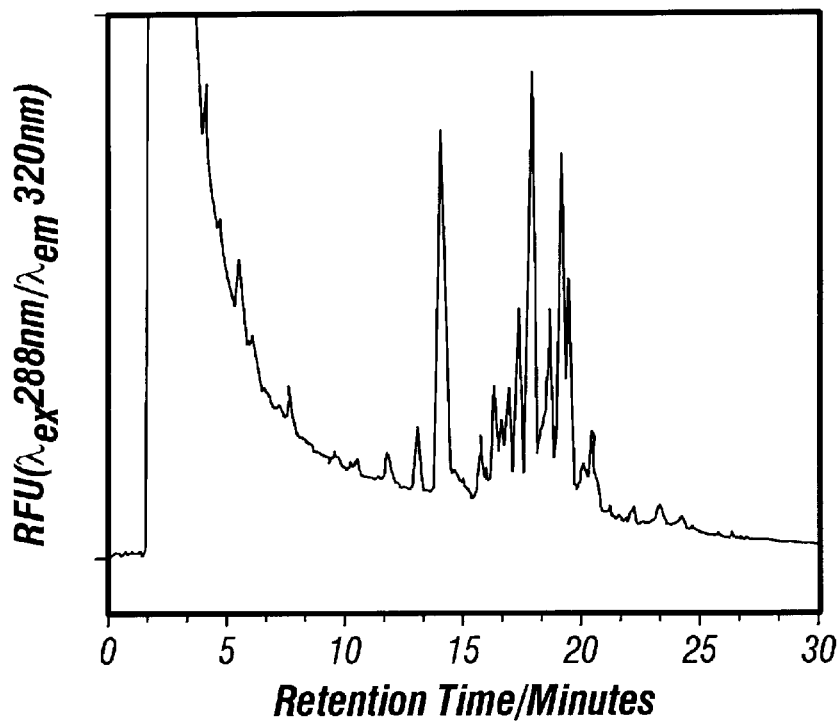
FIG. 16 shows normal phase HPLC analysis of oligosaccharides released from ovalbumin and labelled with (3,4-methylendioxybenzyl)hydroxylamine.
Figure 17:
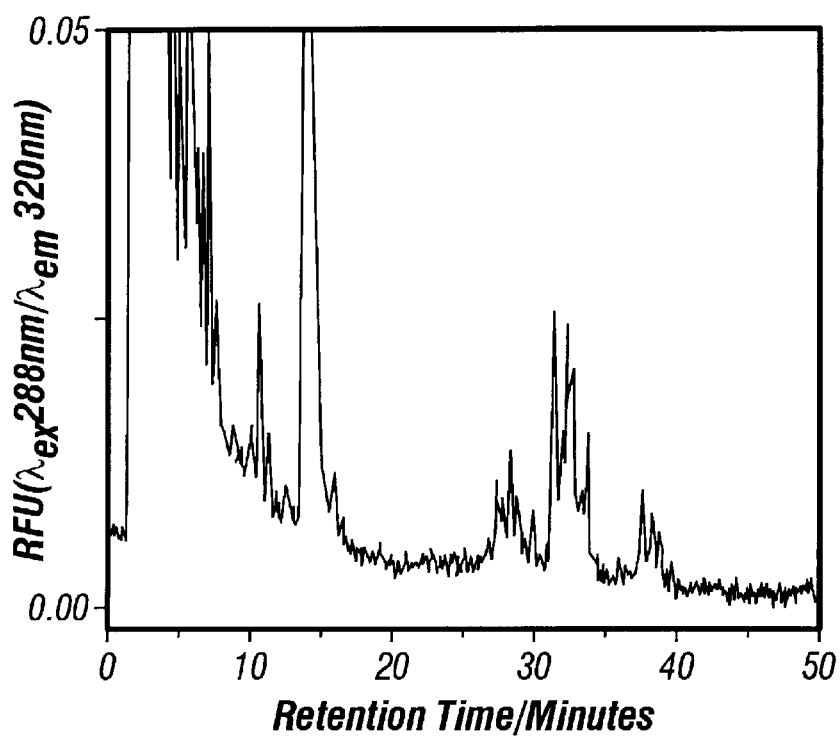
FIG. 17 shows normal phase HPLC analysis of oligosaccharides released from fetuin that have labelled with (3,4-methylendioxybenzyl)hydroxylamine.

The results of labelling of ovalbumin and fetuin are shown in FIGS. 16 and 17, respectively. The column for both separations was an Alltima Armino 250×4.6 mm (Alltech Associates). Binary gradient elution was used. Eluent A was 3% acetic acid/85% acetonitrile titrated to pH 5.8 with triethylamine. Eluent B was 3% acetic acid titrated to pH 5.8 with triethylamine. The gradient was composed of 0% B initially increasing linearly to 85% B at 60 minutes, then increased linearly to 100% B at 64 minutes. Detection was by fluorescence with an excitation wavelength of 288 nm and emission wavelength of 320 nm.

12. Attaching glycan derivatives to supports. It will be appreciated that nitrone chemistry according to the present invention provides a very effective means for the attachment of a reducing sugar to a polymer surface. In this method, a polymer-bound aldehyde group is first converted to a nitrone by reacting it with an excess of hydroxylamine. The immobilised nitrone is then converted to an immobilised N-substituted hydroxylamine by reduction by a reducing agent, such as sodium cyanoborohydride, pyridine-borane or trimethylamine-borane. As an example of this strategy, amino-substituted polystyrene is reductively coupled with an excess of glutaraldehyde to provide a polymer carrying a spacer arm terminated with an aldehyde function. The aldehyde function is then converted to an N-substituted hydroxylamine by reduction with sodium cyanoborohydride in the presence of excess hydroxylamine at pH 4. Alternatively, the aldehyde functionality can be incorporated into amino-substituted polystyrene beads by diazotisation with nitrous acid and azo coupling to a hydroxybenzaldehyde in alkaline solution. More generally, any method of incorporating aldehyde groups into a polymer can be adapted to the preparation of a polymer carrier substituted with N-substituted hydroxylamine groups. Examples for the incorporation of aldehyde groups include the partial oxidation of polysaccharides with periodate and the specific oxidation of galactose-containing polymers (such as agarose) with galactose oxidase enzyme.

The advantage of preparing such polymers substituted with N-substituted hydroxylamine groups is the ease with which they can be used to immobilise reducing sugars under mild conditions of pH and temperature, such as those described above for the labelling of reducing sugars.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

R. A. Evangelista, A. Guttman and F.-T. A. Chen, Acid-catalysed reductive amination of aldoses with 8-aminopyrene-1,3,6-sulfonate, Electrophoresis, 1996, 17, 347–351.

H. Paulsen and M. Butzis, Darstellung von acyclischen und cyclischen Kohlenhydrat-nitronen, Chem. Ber., 1974, 107, 1998–2008.

A. S. Kende and J. S. Mendoza, Tetrahedron Letters, 1991, Vol. 32, No. 14, 1699–1702.

J. Suzuki, A. Kondo, I. Kato, S. Hase, T. Ikenaka Clin. Chem., 1992, 38, 752–755.

What is claimed is:

1. A method for producing a glycan nitrone comprising reacting a glycan with a mono-N-substituted hydroxylamine at pH 6 or greater to form a glycan nitrone.

2. The method according to claim 1 wherein the reaction is carried out at pH 6.5 or greater.

3. The method according to claim 1 wherein the mono-N-substituted hydroxylamines are selected from benzylic N-substituted hydroxylamines and N-arylhydroxylamines.

4. The method according to claim 3 wherein the benzylic N-substituted hydroxylamines are prepared by reduction of oximes obtained by reaction of aromatic aldehydes with hydroxylamine.

5. The method according to claim 4 wherein the benzylic N-substituted hydroxylamine is N-(3-methoxylbenzyl) hydroxylamine prepared from 3-methoxybenzaldehyde.

6. The method according to claim 4 wherein the benzylic N-substituted hydroxylamine is N-(3,4-methylenedioxybenzyl)hydroxylamine prepared from piperonal.

7. The method according to claim 3 wherein the benzylic N-substituted hydroxylamines are prepared by alkylation of hydroxylamine using an excess of a benzyl halide, with formation of an N,N-disubstituted hydroxylamine, from which one of the aralkyl substituents is removed by mild oxidation followed by hydrolysis.

8. The method according to claim 3 wherein the N-arylhydroxylamines are prepared by reduction of corresponding nitro compounds or oxidation of corresponding primary amines.

9. The method according to claim 8 wherein the N-arylhydroxylamine is N-phenylhydroxylamine produced by reduction of nitrobenzene.

10. The method according to claim 8 wherein the N-arylhydroxylamines are prepared by oxidation of the corresponding amines using samarium diiodide as oxidant.

11. A method for producing a hydroxylamine glycan derivative comprising reacting a glycan nitrone produced by the method according to claim 1 with a reducing agent to form a hydroxylamine glycan derivative.

12. The method according to claim 11 wherein the reducing agent is sodium cyanoborohydride.

13. The method according to claim 11 wherein the glycan nitrone is bound to a polymer.

14. The method according to claim 13 wherein the glycan nitrone is bound to a polymer via a mono-N-substituted hydroxylamine.

15. The method according to claim 11 wherein the glycan nitrone is produced from a biomolecule selected from the group consisting of a monosaccharide, a polysaccharide, and an oligosaccharide released from a glycoprotein.

16. The method according claim 11 wherein the hydroxylamine glycan derivative is treated to form one or more carbonyl groups.

17. The method according to claim 16 wherein the treatment of the glycan to form the carbonyl group or groups is selected from the group consisting of chemical treatment and enzymatic treatment.

18. The method according to claim 17 wherein the chemical treatment is by periodate oxidation, or deamination using nitrous acid.

19. The method according to claim 17 wherein the enzymatic treatment is with galactose oxidase.

20. The method according to claim 11 wherein the glycan nitrone includes a detectable label.

21. The method according to claim 20 wherein the detectable label is selected from a label which confers ultraviolet-absorbing or fluorescent properties.

* * * * *